United States Patent
Van Der Knaap et al.

(10) Patent No.: US 10,736,286 B2
(45) Date of Patent: Aug. 11, 2020

(54) *SPATHIPHYLLUM* HAVING REDUCED POLLEN CONTENT AND METHOD FOR THE PREPARATION THEREOF

(71) Applicant: KP Holland Licensing B.V., Naaldwijk (NL)

(72) Inventors: Adrianus Leonardus Josef Van Der Knaap, Naaldwijk (NL); Timothy Johan Herman Hoogkamp, Naaldwijk (NL)

(73) Assignee: KP HOLLAND LICENSING B.V., Naaldwijk (NL)

( * ) Notice: Subject to any disclaimer, the term of this patent is extended or adjusted under 35 U.S.C. 154(b) by 73 days.

(21) Appl. No.: 15/782,201

(22) Filed: Oct. 12, 2017

(65) Prior Publication Data
US 2018/0098517 A1    Apr. 12, 2018

(30) Foreign Application Priority Data
Oct. 12, 2016   (EP) .................................... 16193542

(51) Int. Cl.
*A01H 5/02* (2018.01)
*A01H 1/02* (2006.01)

(52) U.S. Cl.
CPC ................. *A01H 5/02* (2013.01); *A01H 1/02* (2013.01)

(58) Field of Classification Search
CPC ....................................................... A01H 5/02
See application file for complete search history.

(56) References Cited

U.S. PATENT DOCUMENTS

| PP9,958 P | * | 7/1997 | Cornelis |
| PP10,008 P | | 8/1997 | Osiecki |
| PP26,759 P2 | | 5/2016 | Van Der Knaap |

OTHER PUBLICATIONS

Eeckhaut, T., et al. Plant Cell, Tissue and Organ Culture; 2004, vol. 78: pp. 241-246.*
Van Der Knaap "Pollen free *Spathiphyllum* shows no aging" newPlantsand Flowers, published on the internet Jul. 16, 2012 pp. 1-2.*
Eeckhaut, T., et al. Plant Cell, Tissue and Organ Culture; 2004, vol. 78: pp. 241-246. (Year: 2004).*
Eeckhaut, T., el al. Plant Cell, Tissue and Organ Culture; 2004, vol. 78: pp. 241-246. (Year: 2004).*
Van Der Knaap "Pollen-free *Spathiphyllum* shows no aging" newPlantsandFlowers, Jun. 16, 2012, 2 pages.
Vanstechelman et al., "Morphological and Anatomical Characterisation of Chemically Induced Polyploids in Spathiphyllum wallisii" ISHS Acta Horticulturae 836: XXIII International Eucarpia Symposium, Section Ornamentals: Colourful Breeding and Genetics, 2009, p. 79-84.
Ogawawara et al., "Artificial Induction of Tetraploid Plants via Colchicine Treatment and Apical Meristem Culture in Spathiphyllum wallisii Regel 'Merry'" Hort.Res.(Japan)) 11(2):189-194.2012.
Acuna et al., "Apospory followed by sterility in a hypotriploid hybrid (2x× 4x) of Paspalum" Caryologia, vol. 57, No. 4:373-378,2004.

* cited by examiner

*Primary Examiner* — Russell Kallis
(74) *Attorney, Agent, or Firm* — Browdy and Neimark, PLLC

(57) ABSTRACT

The invention relates to *Spathiphyllum* plants having reduced pollen content, obtained by a method, comprising the steps of providing a tetraploid *Spathiphyllum* parent and a diploid *Spathiphyllum* parent, and crossing these tetraploid and diploid parents to produce the *Spathiphyllum* plants having reduced pollen content. The invention also relates to a method for producing *Spathiphyllum* plants having reduced pollen content.

18 Claims, 6 Drawing Sheets

SPATHIPHYLLUM HAVING REDUCED POLLEN CONTENT AND METHOD FOR THE PREPARATION THEREOF

CROSS REFERENCE TO RELATED APPLICATIONS

This application claims the benefit of European application Ser. No. 16193542.4, filed Oct. 12, 2016 which is incorporated herein by reference in its entirety.

FIELD

The invention relates to *Spathiphyllum* having reduced pollen content, to progeny thereof and to a method for the preparation of such *Spathiphyllum*.

BACKGROUND

*Spathiphyllum* is a genus of about 40 species of monocotyledonous flowering plants in the family Araceae, native to tropical regions of the Americas and southeastern Asia. *Spathiphyllum* plants are evergreen herbaceous perennial plants with large leaves having a length of 12-65 cm and width of 3-25 cm. The flowers are produced in a spadix, surrounded by a 10-30 cm long, white, yellowish, or greenish spathe. Leaves are basal, glossy and somewhat deeply veined, ovate and acuminate. The petioles are long and the leaves arch gracefully. The plant produces offsets at the base and in time becomes a dense clump. The plants do not need large amounts of light or water to survive.

For the above reasons, *Spathiphyllum*, in particular smaller species thereof are extremely attractive as indoor ornamental plants.

However, at the spadix, *Spathiphyllum* produces a large amount of pollen. As the spadix is very exposed to the environment, the pollen are readily distributed, resulting the leaves being covered by pollen, by which the plant gets a less attractive appearance. Also, the pollen can stain textiles, such as human clothes when getting in contact therewith. Further, thrips are attracted to the pollen of *Spathiphyllum*, resulting in plagues that may cause significant damage, in particular for *Spathiphyllum* growers. Therefore, the use of biocides can be reduced in *Spathiphyllum* with reduced pollen content or even minimized in pollen-free *Spathiphyllum*.

SUMMARY

Therefore, it is an object of the present invention to provide *Spathiphyllum* with a reduced pollen content.

In the art, it has hitherto been impossible to provide for *Spathiphyllum* with reduced pollen content in a controllable manner. Only by spontaneous mutations, such plants may be generated. However, such mutations are uncontrolled and result, almost without exception, in plants with undesired characteristics that make such plants commercially unattractive.

Accordingly, the *Spathiphyllum* cultivar "Sensation" of the company Oglesby which has a reduced pollen content is known in the art, but it has never been observed that reduced pollen content was linked to a triploid background of the cultivar. The cultivar "Sensation" appears to be a spontaneous mutation and has less attractive characteristics, such as the fact that the architecture of the plant is irregular, the leaves are large, often irregular, and flowering does not take place often. The plant is primarily marketed as a green flowerless plant.

The inventors have surprisingly found that in *Spathiphyllum* plants, triploidy coincides with significant reduction or complete lack of pollen. While breeding *Spathiphyllum*, the present inventors observed some pollen free mutants as a result of spontaneous mutations. By further investigating the genetic background of said mutants, it was surprisingly observed that the said mutants shared triploidy. Although it is known that triploid plants can usually not be propagated sexually, it was not known that triploidy can coincide with the complete lack of pollen in *Spathiphyllum*.

In the art, attempts have been made to produce polyploid *Spathiphyllum*. Vanstechelman et al. (Acta Hortic. (2009) 836, 79-84, DOI: 10.17660/ActaHortic.2009.836.10, http://dx.doi.org/10.17660/ActaHortic.2009.836.10) describe the production of tetraploid *Spathiphyllum wallisii*, that however resulted in less attractive *Spathiphyllum* plants, with aberrant leaf form, decreased number of leaves, shoots and flowers as compared to the diploid counterpart. Controlled preparation of triploid *Spathiphyllum* plants, i.e. without relying on spontaneous mutations, that are commercially of interest, has never been described, nor are such plants characterized.

The inventors therefore provide for the first time a *Spathiphyllum* plant with reduced pollen content, obtained by a method, comprising the steps of
 a) providing a tetraploid *Spathiphyllum* parent,
 b) providing a diploid *Spathiphyllum* parent,
 c) crossing the parents of a) and b) to produce *Spathiphyllum* plant with reduced pollen content.

DESCRIPTION

By crossing a tetraploid *Spathiphyllum* parent with a diploid *Spathiphyllum* parent, triploid *Spathiphyllum* offspring can be produced, that have reduced pollen content or are even pollen free. For the first time, reduced pollen or pollen free *Spathiphyllum* can be provided in a controlled manner by the above crossing. The skilled person is capable to perform crossings between both parents, e.g. by using a small brush to collect pollen from the male parent and to fertilize the female parent therewith.

The term 'reduced pollen content' is to be understood as the fact that the pollen content of the crossing of step c) comprises less pollen, both overall as well as per mature inflorescence, i.e. per spadix of a mature flower, as compared to that of the tetraploid *Spathiphyllum* parent of step a) and of the diploid *Spathiphyllum* parent of step b). The term 'reduced pollen *Spathiphyllum*' is intended to mean a *Spathiphyllum* plant having such reduced pollen content. In particular, said content is less than 50% of the pollen of each of both parents, preferably less than 35%, more preferably less than 25%, even more preferably less than 10%, 5% 2% or 1%. Most preferably, the crossing of step c) is completely pollen free.

Tetraploid *Spathiphyllum* plants are known, such as e.g. described by Vanstechelman, supra, and literature cited therein. In the art, methods are known to prepare tetraploid plants, starting from diploid progenitors, e.g. by using antimitotic agents.

In order to arrive at commercially attractive *Spathiphyllum* with reduced pollen content or pollen free *Spathiphyllum*, the tetraploid parent is preferably capable of developing at least 3, more preferably at least 4 shoots in a period of two months after the it reaches, as juvenile plantlet, a length of 5 cm and potted in potting soil and kept in the greenhouse at a temperature of 20-22° C. at a humidity of 50-80%. Said shoots preferably grow from the plant base, and not from an internode on another shoot. Each of the said 3 or 4 shoots therefore preferably has a single node without internodes being present thereon. In case the tetraploid parent develops less than 3 shoots in the period of two months after the juvenile plantlet reaches a length of 5 cm, the triploid offspring will usually not be capable to produce sufficient shoots from the plant base.

The mature leaves, i.e. from plants carrying flowers, of the tetraploid *Spathiphyllum* parent preferably have a length to width ratio of at least 1.9. Tetraploid *Spathiphyllum* plants often suffer from aberrant leaf form, such as broad leaves, which can be inherited by the offspring, and not compensated by the diploid second parent. Therefore, in order to provide triploid offspring with attractive stretched leaf form, the length to width ratio of the leaves of the mature tetraploid parent, as measured as described in Vanstechelman, supra, is preferably at least 1.9.

For similar reasons as explained above, the mature leaves of the tetraploid *Spathiphyllum* parent preferably have a thickness of more than 0.23 mm, more preferably of more than 0.25 mm, even more preferably more than 0.30. Said parameters can e.g. be measured as described in Vanstechelman, supra.

In order to avoid aberrant leaf form, the width of each leaf of the tetraploid *Spathiphyllum* parent preferably continuously increases from the leaf tip to a maximum at about half the length of the leaf, measured from the leaf tip to the leaf stem, and continuously decreasing from the said maximum towards the said leaf stem. Such a leaf form, where the width gradually increases to a maximum at about half way of the leaf and decrease as from there, provides for an attractive regular shape, also in the triploid offspring.

The tetraploid *Spathiphyllum* parent is preferably obtained by a method that comprises the following steps:
 i) treating *Spathiphyllum* plantlets or plant parts with an antimitotic agent,
 ii) allowing the plantlets of step i) to grow in a first growth medium,
 iii) removing part of the plantlets of step ii),
 iv) allowing the plantlets parts of step iii) to grow in a second growth medium to generate plantlets with new shoots and leaves,
 v) repeating steps iii) and iv) for 0 to 4 times in the second or a further growth medium,
 vi) determining the ploidy of the plantlets obtained in step iv) and/or v),
 vii) selecting tetraploid plantlets of step vi),
 viii) allowing the selected plantlets of step vii) to grow to mature plants.

Antimitotic treatment of diploid plants to produce plants with a double chromosome number is well established in the art. Suitable antimitotic agents are also known in the art, such as e.g. colchicine, oryzalin or trifluralin. A plant part, such as a single major shoot with a sturdy base can be immersed in a medium comprising the antimitotic agent, such as an aqueous 1 w/w % colchicine solution. Said shoot is preferably 1-2 cm in height and void of leaves and roots. However, other plant parts, such as e.g. anther filaments can also be used. Such a treatment results in one or more of the cells of the plant part to become tetraploid. After being contacted with the antimitotic agent, e.g. for 2-24 hours, the plant parts can be rinsed with water and incubated on or in a first growth medium. The skilled person will be aware of a proper growth medium that comprises the necessary nutrients, trace elements and plant vitamins. The said first growth medium preferably comprises plant growth regulators such as cytokines for shoot growth induction and auxins for root growth induction. A suitable cytokine is benzylaminopurine, whereas a suitable auxin is indole-3-butyric acid. The skilled person will be capable of determining the proper growth medium and concentrations of the compounds therein, such as MS medium (Murashige and Skoog (1962) Physiol Plant 15(3): 473-497). The medium is preferably a gel, on which the plant parts are placed, the cut base portion being in contact with the gel medium, allowing leaves to develop from the shoots and new shoots and roots from the cut base. Said step ii) usually takes 4 to 6 weeks.

In order to produce a plant of unitary genetic background, i.e. the genome of all the cells being identical, and in particular being tetraploid, a part of the grown plantlet is taken and inoculated in or on a second growth medium, allowing the plantlet part to develop into plantlets with new shoots and leaves, and possibly also new roots. This step iv) usually takes 4 to 6 weeks, like step ii). In particular, new shoots, growing from the base are taken to grow on the second medium. The second medium preferably corresponds with the first medium, but preferably contains less, preferably 2 to 6 times less, in particular 3 to 5 or about 4 times less of the cytokines and auxins as compared to the first growth medium. However, the second medium can be identical to the first medium in case multiplication is observed to drop.

In order to obtain plants with unitary genetic background, the latter two steps of removing a part of the plantlets grown in or on the first medium and allowing said parts to grow on a second growth medium can be repeated 0 to 4 times. With "0" times it is meant that no repeat of said steps take place. In that case, step v) above does not exist. Said steps are repeated in order to obtain a unitary genetic background. Upon repeating the steps, the second medium can be used, or a similar medium wherein the levels of cytokines and/or auxins are further limited.

The ploidy of the plantlets, growing in or on a growth medium can be determined in order to check whether the plantlet is tetraploid or at least comprises tetraploid cells. In the art, methods to determine the ploidy are known, such as e.g. described and referred to in Vanstechelman, supra.

Accordingly, tetraploid plants are selected and allowed to grow to mature plants, which can be used as tetraploid parent to produce the envisaged reduced pollen or pollen free *Spathiphyllum* plant. Such a mature tetraploid plant is preferably selected as a potential parent, based on the above criteria of number of shoots, leaf form and thickness.

At the end of or after step iv) or v) or both steps, i.e. after 4 to 6 weeks growth on a growth medium, preferably a selection is made of plantlets having one or more, preferably all of the following criteria:
 a size of at least 3 cm from the plant base,
 having at least 3 leaves formed at the said plant base without internodes,
 the leaves being free of brown and yellow discolouring,
 the width of each leaf continuously increasing from the leaf tip to a maximum at about half the length of the leaf, measured from the leaf tip to the leaf stem, and continuously decreasing from the said maximum towards the said leaf stem.

Such plantlets are good candidates to be tetraploid, having the envisaged characteristics. It is also possible to perform a similar selection at the end or after step ii). It is to the be noted that the number of shoots as explained above is preferably measured two months after such plantlet is potted in potting soil and allowed to grow in a greenhouse under conditions as described above.

In order to produce reduced pollen or pollen free *Spathiphyllum* of commercial interest, i.e. having significant ornamental value, the diploid *Spathiphyllum* parent is preferably capable of developing at least 10, more preferably at least 15 shoots in a period of two months after the it reaches, as juvenile plantlet, a length of 5 cm and potted in potting soil and kept in the greenhouse at a temperature of 20-22° C. at a humidity of 50-80%. Using such a diploid parent, it is possible to compensate in the triploid offspring, for the relatively low number of shoots present in the tetraploid parent. Of course, it is envisaged to use a tetraploid parent with as much shoots as possible, but tetraploid *Spathiphyllum* usually develops less than 5 shoots in a period of two months after the it reaches, as juvenile plantlet, a length of 5 cm and potted in potting soil and kept in the greenhouse at a temperature of 20-22° C. at a humidity of 50-80%.

The diploid *Spathiphyllum* parent preferably has leaves with a length to width ratio of at least 2.5. The leaf thickness is of less importance for the diploid parent.

Also, the diploid parent preferably has regular leaves, i.e. the width of each leaf of the diploid *Spathiphyllum* parent continuously increasing from the leaf tip to a maximum at about half the length of the leaf, measured from the leaf tip to the leaf stem, and continuously decreasing from the said maximum towards the said leaf stem.

Attractive *Spathiphyllum* plants with reduced pollen content can be obtained when the diploid parent fulfills one or more, preferably all, of the above criteria.

By crossing a tetraploid *Spathiphyllum* female parent plant as described above with a male diploid *Spathiphyllum* parent plant, or the reciprocal, a reduced pollen of pollen free *Spathiphyllum* plant with desired properties can be obtained in a controlled fashion, and attractive reduced pollen or pollen free *Spathiphyllum* plants can be obtained, having one or more, preferably all of the following characteristics:

developing at least 5 shoots in a period of two months after the it reaches, as juvenile plantlet, a length of 5 cm and potted in potting soil and kept in the greenhouse at a temperature of 20-22° C. at a humidity of 50-80%,
the mature plant having leaves with a length to width ratio of 2.2 or more
the mature leaves of the plant having a thickness of below 0.25 mm,
the width of each leaf thereof continuously increasing from the leaf tip to a maximum at about half the length of the leaf, measured from the leaf tip to the leaf stem, and continuously decreasing from the said maximum towards the said leaf stem.

In a preferred embodiment, the tetraploid parent of step a) and the diploid parent of step b) are chosen from the group, consisting of the *Spathiphyllum* species *S. floribundum, S. wallisii, S. cochlearispathum, S. montanum* and *S. silvicola*, and more preferably belong to the same species. However, the tetraploid parent should preferably not originate from the same diploid plant that is used as diploid parent in order to avoid inbred.

Also described and claimed is progeny of the reduced pollen or pollen free *Spathiphyllum* plant as described herein. As triploid plants are usually infertile as a result of their odd chromosome number, Progeny from triploid plants can be obtained e.g. by subjecting the triploid *Spathiphyllum* of the invention to treatment with an antimitotic agent, as described above for the preparation of tetraploid plants from a diploid progenitor. This results in a hexaploid *Spathiphyllum* plant that can be crossed with e.g. a diploid plant, resulting in new tetraploids, having new characteristics crossed in through the diploid parent. Such offspring, as well as asexually reproduced offspring obtained by cutting off plant parts and regenerating complete new mature plants are also encompassed. The said tetraploid offspring can also be used to generate a new generation of triploid offspring by crossing the said tetraploid with a diploid parent.

Also described and claimed is a method for the preparation of a reduced pollen or pollen free *Spathiphyllum* plant as described herein, comprising the steps of:

a) preparing a tetraploid parent, comprising the step of treating *Spathiphyllum* plantlets or plant parts with an antimitotic agent,
) crossing the tetraploid parent of step a) with a diploid parent, to produce the *Spathiphyllum* plant with reduced pollen content.

Step a) is preferably performed as described above, and the tetraploid parent and the diploid parent are preferably as described above. However, it is also possible to produce a triploid *Spathiphyllum* plant by using unreduced, i.e. diploid gametes, obtained by a disrupted meiosis in a diploid parent, and combine these with monoploid gametes, obtained by regular meiosis in a regular diploid plant. The skilled person is aware of suitable techniques to obtain diploid gametes and to combine with monoploid gametes.

The skilled person will be aware of suitable conditions to develop and grow the plants as described above. Preferably, the plants are grown in a greenhouse at a temperature of 20-22° C. at a humidity of 50-80%. The in vitro methodology described herein, i.e. the colchicine treatment and the development of plantlets via tissue culture as described above e.g. for the preparation of tetraploid plants is preferably performed at ambient temperature a laboratory conditions, i.e. at 20-24° C. and a humidity of 40-70% outside, and 80-90% inside containers such as petridishes closed with a lid, partly or completely under sterile conditions.

The claimed reduced pollen or pollen free *Spathiphyllum* plants and methods for the preparation thereof will be illustrated by the following examples and figures.

EXPERIMENTAL

Example 1

Preparation of a Tetraploid Parents

Figure 1A:
FIG. 1A: Diploid *Spathiphyllum* Bingo Cupido™ 'Spapril' (CPVO file nr. 20131221) used for the preparation of a tetraploid parent.
Figure 1B:
FIG. 1B: Diploid *Spathiphyllum* Côco Cupido™ 'Spajuni', (CPVO file nr. 20121216) used for the preparation of a tetraploid parent.

It is to be noted that Several diploid *Spathiphyllum* plants were taken as parent or as starting plant for the preparation of a tetraploid patent plants, parents were selected based on the above desired requirements of shoot number and leaf form. Techniques known in the art can be used. As few of many possibilities, diploid *Spathiphyllum* Bingo Cupido™ 'Spapril' (FIG. 1A) and Côco Cupido™ 'Spajuni' (FIG. 1B) were used for the preparation of tetraploid plants. Said mature plants have more than 15 shoots starting from the base, the leaves having a regular form, a length to width ratio of about 2.5, and a leaf thickness of about 2.0 mm. Major shoots of 1.5 cm in height were cut from the mature plant and incubated for 10 hours in a sterile aqueous 1 w/w % colchicine solution and rinsed twice with sterile water at ambient temperature.

Figure 2:
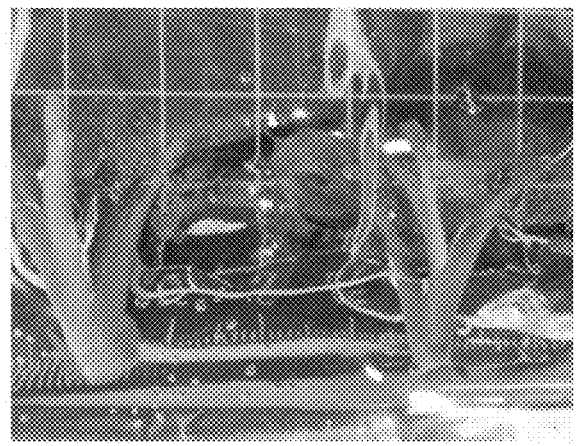
FIG. 2: Single shoots of the *Spathiphyllum* of FIG. 1.
Figure 3:
FIG. 3: plantlets developed from shoots of FIG. 2.

The thus treated shoots were placed in petridishes on a MS gel medium containing 30 g/l sucrose, 2 g/l gellan gum (Gelrite™, Duchefa, Netherlands) 0.5-2.5 mg/l benzylaminopurine and 0.1-0.5 mg/l indole-3-butyric acid, see FIG. 2. The shoots were kept at 22-24° C. and allowed to develop into plantlets with leaves, small clumps of new shoots at the base and roots, see FIG. 3.

Figure 4:
FIG. 4: plantlets derived from parts of the plantlets of FIG. 3.
Figure 5:
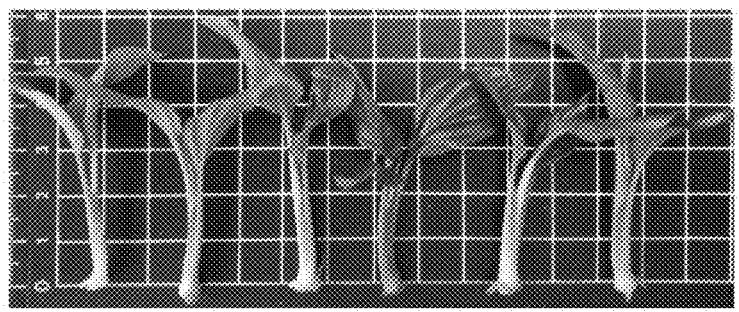
FIG. 5: Selected plantlets of FIG. 4.
Figure 6A:
FIG. 6A: Juvenile tetraploid plants derived from Bingo Cupido™ 'Spapril'.
Figure 6B:
FIG. 6B: Mature tetraploid plant KP07-4-92 derived from Bingo Cupido™ 'Spapril'.
Figure 6C:
FIG. 6C: Mature tetraploid plant KP08-4-97 derived from Côco Cupido™ 'Spajuni'.

After 6 weeks of growth, small clumps (circled in FIG. 3) of said new shoots were taken, separated and individually placed on a second medium, being identical to the first medium, however containing two to six times less benzylaminopurine and indole-3-butyric acid. FIG. 4 shows plantlets after 4 weeks of growth on the second medium. After 6 weeks of growth, again newly developed shoots were taken and grown on a third growth medium, identical to the second growth medium now free of benzylaminopurine but containing 5 to ten times more indole-3-butyric acid. The plantlets were selected on the presence of at least 3 leaves, a height as measured from the base (i.e. where the shoots start growing up and the roots start growing down) of at least 3 cm, absence of discoloration and absence of internodes, see FIG. 5. Samples were taken and the ploidy was determined by flow cytometry, as described in Stechelman, supra. A plurality of tetraploid plantlets were allowed to develop into juvenile plants by transferring the plantlets into potting soil and kept in a greenhouse at a temperature of 20-22° C. and a humidity of 50-80% for two months. Numerous tetraploid offspring was found that developed at least 5 shoots in a period of two months after reaching, as juvenile plantlet, a length of 5 cm and being potted in potting soil and kept in the greenhouse at a temperature of 20-22° C. at a humidity of 50-80%, having a leaf length-to-width ratio of about 2, and a leaf thickness about 0.3 mm. See e.g. FIG. 6A for juvenile tetraploid plants derived from Bingo Cupido™ 'Spapril' For crossing purposes, a plurality of tetraploid juvenile plants were allowed to develop into mature plants with an increased number of shoots and carrying flowers, e.g. of Bingo Cupido™ 'Spapril' being designated KP07-4-92 (FIG. 6B) and of Côco Cupido™ 'Spajuni' being designated KP08-4-97 (FIG. 6C).

A plurality of tetraploid plants were obtained with the characteristics described herein, also by different diploid starting lines.

Example 2

Preparation of *Spathiphyllum* Plants with Reduced Pollen Content

Figure 7:
FIG. 7: Diploid *Spathiphyllum* parent Cupido™ Compacto 'Sparanke' (CPVO file nr. 20081387).
Figure 9A:
FIG. 9A: Triploid pollen free *Spathiphyllum* plant KP15-3-39.
Figure 9B:
FIG. 9B: Detail of the plant of FIG. 9.

Tetraploid (4×) plants of example 1 were crossed with diploid (2×) *Spathiphyllum*. Mature diploid plants were chosen having about 20 shoots starting from the base, the leaves having a regular leaf form, a length to width ratio of about 2.6, and a leaf thickness of about 2.0 mm. Amongst others the following crosses were performed:

The tetraploid originating from Côco Cupido™ 'Spajuni', KP08-4-97 (4×, FIG. 6C) was used as female parent and crossed with diploid Cupido™ Compacto 'Sparanke' (2×) (FIG. 7A). Crossings of male gametes and female gametes were performed in a usual manner as follows. Pollen were taken from a male spadix and contacted with a female spadix using a fine paint brush. A selection on the triploid progeny was made on at least one of the following criteria or a combination of two or more thereof: developing at least 5 shoots in a period of two months after it reaches, as juvenile plantlet, a length of 5 cm and potted in potting soil and kept in the greenhouse at a temperature of 20-22° C. at a humidity of 50-80%, the mature plant having leaves with a length to width ratio of 2.2 or more, a thickness of below 0.25 mm, and regular leaf form (i.e. the width of each leaf continuously increasing from the leaf tip to a maximum at about half the length of the leaf, measured from the leaf tip to the leaf stem, and continuously decreasing from the said maximum towards the said leaf stem). A plurality of triploid offspring was generated, such as KP15-3-39 (FIGS. 9A and 9B). Said offspring was pollen free, i.e. the spadix of the mature flowers being void of pollen. It developed more than 5 shoots after reaching a length of 5 cm as described above, the leaves of the mature plant had a regular form, having a length to width ratio of more than 2.2 and a thickness of less than 0.25 mm.

Figure 8:
FIG. 8: Triploid pollen free *Spathiphyllum* plant KP13-3-28.

In another crossing, the tetraploid originating from Bingo Cupido™ 'Spapril', KP07-4-92 (4×, FIG. 6B) was used as female parent and crossed with diploid Côco Cupido™ 'Spajuni', (2×, FIG. 1B), using the same selection criteria as described above for the selection of triploid offspring. A plurality of triploid offspring was generated, such as pollen-free KP13-3-28 (FIG. 8). Said offspring was pollen free, i.e. the spadix of the mature flowers being void of pollen. It developed more than 5 shoots after reaching a length of 5 cm as described above, the leaves of the mature plant had a regular form, having a length to width ratio of more than 2.2 and a thickness of less than 0.25 mm.

Similar results were obtained with other parental lines, also when reciprocal crossings was performed, i.e. using a female tetraploid parent and a diploid male parent.

The invention claimed is:

1. A mature pollen-free triploid *Spathiphyllum* plant, obtained by a method comprising the steps of:
   a) providing a tetraploid *Spathiphyllum* parent;
   b) providing a diploid *Spathiphyllum* parent;
   c) crossing the parents of a) and b) to produce an infertile triploid *Spathiphyllum* plant; and
   d) allowing the triploid plant to grow to maturity to produce the mature pollen-free triploid *Spathiphyllum* plant.

2. The mature pollen-free triploid *Spathiphyllum* plant of claim 1, wherein the tetraploid *Spathiphyllum* parent provided in step a) is one that develops at least 3 shoots in a period of two months after it reaches, as juvenile plantlet, a length of 5 cm and potted in potting soil and kept in a greenhouse at a temperature of 20-22° C. at a humidity of 50-80%.

3. The mature pollen-free triploid *Spathiphyllum* plant of claim 1, wherein the tetraploid *Spathiphyllum* parent provided in step a) is one in which:
the mature leaves have a length to width ratio of at least 1.9; and/or
the mature leaves have a thickness of at least 0.23 mm, and/or
the width of each leaf continuously increases from the leaf tip to a maximum at about half the length of the leaf, measured from the leaf tip to the leaf stem, and continuously decreases from the said maximum towards the said leaf stem.

4. The mature pollen-free triploid *Spathiphyllum* plant of claim 1, wherein the tetraploid *Spathiphyllum* parent provided in step a) is one that is obtained by:
i) treating *Spathiphyllum* plantlets or plant parts of *Spathiphyllum* plantlets with an antimitotic agent,
ii) allowing the plantlets of step i) to grow in a first growth medium,
iii) removing part of the plantlets of step ii),
iv) allowing the plantlets part of step iii) to grow in a second growth medium to generate plantlets with new shoots and leaves,
(v) repeating steps iii) and iv) for 0 to 4 times in the second or a further growth medium,
(vi) determining the ploidy of the plantlets obtained in step iv) and/or v),
(vii) selecting tetraploid plantlets of step vi), and
(viii) allowing the selected plantlets of step vii) to grow to mature plants.

5. The mature pollen-free triploid *Spathiphyllum* plant of claim 4, wherein the process of obtaining the tetraploid *Spathiphyllum* parent further includes the step of (1) selecting, after step iv) or v) or both, plantlets of a size of at least 3 cm from the plant base, having at least 3 leaves formed at the said plant base without internodes, the leaves being free of brown and yellow discoloring, the width of each leaf continuously increasing from the leaf tip to a maximum at about half the length of the leaf, measured from the leaf tip to the leaf stem, and continuously decreasing from the said maximum towards the said leaf stem, and the determining step (vi) is conducted on the plantlets selected in said step (1).

6. The mature pollen-free triploid *Spathiphyllum* plant of claim 1, wherein the diploid *Spathiphyllum* parent of step b) is one which:
develops at least 10 shoots in a period of two months after the it reaches, as juvenile plantlet, a length of 5 cm and potted in potting soil and kept in a greenhouse at a temperature of 20-22° C. at a humidity of 50-80%, and/or
have leaves with a length to width ratio of at least 2.5, and/or
has mature leaves with a thickness of less than 0.25 mm, and/or
has leaves each of which have a width continuously increasing from the leaf tip to a maximum at about half the length of the leaf, measured from the leaf tip to the leaf stem, and continuously decreasing from the said maximum towards the said leaf stem.

7. The mature pollen-free triploid *Spathiphyllum* plant of claim 1, that develops at least 5 shoots in a period of two months after the it reaches, as juvenile plantlet, a length of 5 cm and potted in potting soil and kept in a greenhouse at a temperature of 20-22° C. at a humidity of 50-80%.

8. The mature pollen-free triploid *Spathiphyllum* plant of claim 1, wherein the plant has leaves with a length to width ratio of 2.2 or more.

9. The mature pollen-free triploid *Spathiphyllum* plant of claim 1, wherein the leaves of the plant have a thickness of below 0.25 mm.

10. The mature pollen-free triploid *Spathiphyllum* plant of claim 1, wherein the width of each leaf thereof continuously increases from the leaf tip to a maximum at about half the length of the leaf, measured from the leaf tip to the leaf stem, and continuously decreases from the said maximum towards the said leaf stem.

11. The mature pollen-free triploid *Spathiphyllum* plant of claim 1, wherein the tetraploid parent of step a) and the diploid parent of step b) are selected from the group consisting of the *Spathiphyllum* species *S.floribundum, S.wallisii, S.cochlearispathum, S.montanum* and *S.silvicola*.

12. Triploid pollen-free progeny of the mature pollen-free triploid *Spathiphyllum* plant of claim 1.

13. A method for the preparation of a mature pollen-free triploid *Spathiphyllum* plant, comprising:
a) crossing a tetraploid *Spathiphyllum* parent with a diploid *Spathiphyllum* parent, thereby producing a triploid *Spathiphyllum* plant; and
b) allowing the triploid *Spathiphyllum* plant to grow to maturity, thereby producing the mature pollen-free triploid *Spathiphyllum* plant.

14. The method in accordance with claim 13, further including the steps of preparing said tetraploid *Spathiphyllum* parent by treating *Spathiphyllum* plantlets or plant parts of *Spathiphyllum* plantlets with an antimitotic agent, allowing the treated plantlets to grow to mature plants, and selecting from said mature plants those that are tetraploid.

15. A triploid pollen-free *Spathiphyllum* plant.

16. Triploid pollen-free progeny of the triploid pollen-free *Spathiphyllum* plant of claim 15.

17. An infertile mature pollen-free triploid *Spathiphyllum* plant that is the progeny of a tetraploid *Spathiphyllum* parent and a diploid *Spathiphyllum* parent.

18. Triploid pollen-free progeny of the triploid pollen-free *Spathiphyllum* plant of claim 17.

\* \* \* \* \*